(12) United States Patent
Scopton

(10) Patent No.: US 6,851,424 B2
(45) Date of Patent: Feb. 8, 2005

(54) MOUTHGUARD HAVING DEVICE SECURING TAB

(75) Inventor: Paul Scopton, Winchester, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 71 days.

(21) Appl. No.: 10/217,266

(22) Filed: Aug. 8, 2002

(65) Prior Publication Data

US 2004/0025887 A1 Feb. 12, 2004

(51) Int. Cl.[7] .......................... A61M 16/00; A61C 5/14
(52) U.S. Cl. ................... 128/200.26; 128/859
(58) Field of Search .................. 128/859–862, 128/200.26, 206.29, 207.14, 207.15, 207.17, DIG. 26; 606/108; 600/237–240; 604/171, 179, 264, 270; 602/902

(56) References Cited

U.S. PATENT DOCUMENTS

| 4,185,639 | A | | 1/1980 | Linder | |
|---|---|---|---|---|---|
| 5,009,227 | A | | 4/1991 | Nieuwstad | |
| 5,174,284 | A | * | 12/1992 | Jackson | 128/200.26 |
| 5,590,643 | A | * | 1/1997 | Flam | 128/200.26 |
| 5,806,516 | A | * | 9/1998 | Beattie | 128/207.17 |
| 6,096,009 | A | | 8/2000 | Windheuser et al. | |
| 6,257,238 | B1 | * | 7/2001 | Meah | 128/859 |
| 6,318,371 | B1 | * | 11/2001 | Tyszkiewicz | 128/859 |
| 6,408,850 | B1 | | 6/2002 | Sudge | |
| 6,474,332 | B2 | * | 11/2002 | Arndt | 128/200.26 |
| 6,517,549 | B1 | * | 2/2003 | Dennis | 606/108 |
| 6,533,761 | B2 | * | 3/2003 | Bertoch et al. | 604/174 |
| 6,634,359 | B1 | * | 10/2003 | Rudy et al. | 128/207.14 |
| 6,655,960 | B2 | * | 12/2003 | Fischer | 433/140 |
| 2002/0162555 | A1 | * | 11/2002 | West et al. | 128/206.29 |

FOREIGN PATENT DOCUMENTS

| WO | WO 01/91838 | 5/2001 |
|---|---|---|
| WO | WO 01/62325 A1 | 8/2001 |
| WO | WO 02/076541 A1 | 10/2002 |

OTHER PUBLICATIONS

E-Z-EM, Inc., <http://www.ezem.com/gastroenterology/ezguard.asp?action=gastroenterology>, (accessed Nov. 6, 2002), 2 pages.

US Endoscopy, <http://www.usendoscopy.com/biteb.htm>, (assessed Nov. 6, 2002), 2 pages.

<http://www.endoscopepartsplus.com/SABB942.gif>, (accessed Apr. 15, 2003), 1 page.

* cited by examiner

Primary Examiner—Henry Bennett
Assistant Examiner—Teena Mitchell
(74) Attorney, Agent, or Firm—Christensen O'Connor Johnson Kindness PLLC

(57) ABSTRACT

A mouthguard for allowing medical instruments to be passed into a patient includes an integrally formed or removable locking device. The locking device includes one or more mechanisms for preventing the movement of a guidewire or other medical devices during a surgical procedure.

8 Claims, 2 Drawing Sheets

MOUTHGUARD HAVING DEVICE SECURING TAB

FIELD OF THE INVENTION

The present invention relates to medical devices and in particular to minimally invasive medical devices.

BACKGROUND OF THE INVENTION

As an alternative to conventional surgical techniques, many new minimally invasive techniques are being developed to access and treat internal body tissue. These minimally invasive techniques are generally less traumatic to the patient and heal faster than conventional surgeries.

In many minimally invasive surgical procedures, it is necessary for an endoscopist to route a guidewire from a position outside the patient's body to the position of the tissue to be treated. With the guidewire in place, catheters or devices can be advanced over the guidewire in order to position them adjacent the tissue in question.

For example, in treating the digestive tract, an endoscope is first routed through a patient's alimentary canal and a guidewire is then routed through a lumen in the endoscope in order to position it near the tissue in question. The endoscope is then removed over the guidewire thereby leaving the guidewire at the desired location. Other devices or catheters can then be routed over the guidewire in order to perform a treatment operation. Typically, the proximal end of the guidewire extends out the patient's mouth. In order to avoid having to reposition the guidewire, it is important that the guidewire not be moved during the surgical procedure.

SUMMARY OF THE INVENTION

To aid in securing the position of a guidewire or other medical device that extends out of a patient's mouth during a medical procedure, the present invention is a mouthguard having a tube through which medical devices may be passed. A flange on the tube prevents the mouthguard from being swallowed, and a locking device is either integrally formed or removably secured to the mouthguard. The locking device has mechanisms for securing one or more of the medical devices in position during a medical procedure.

In one embodiment of the invention, the locking device comprises a tab having a slot into which a guidewire or other medical device can be held with a friction fit. Alternatively, the mechanisms can comprise clips, tabs, hook and loop tape or other mechanisms that prevent a guidewire or other device from being moved during surgery.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENTS

Figure 1:
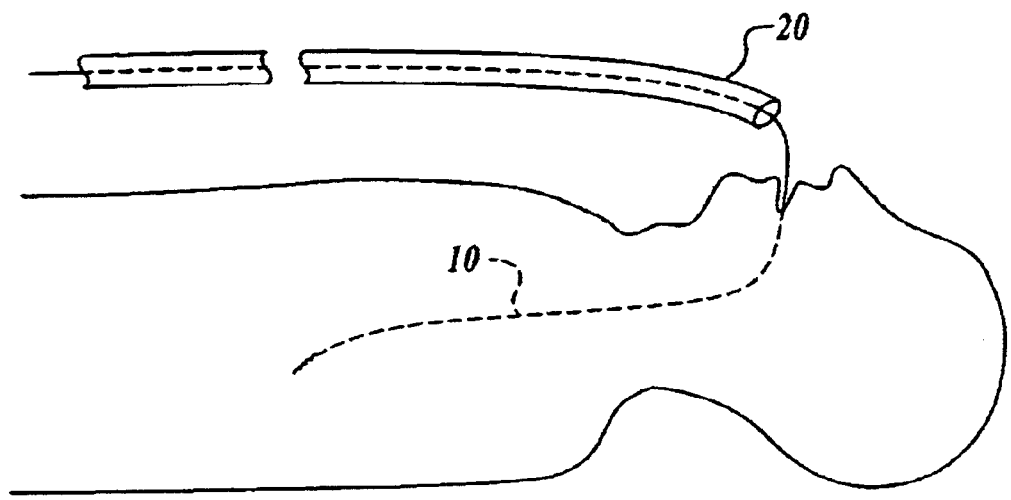
FIG. 1 illustrates a patient undergoing a catheter-based surgical procedure with a conventional catheter and guidewire.
Figure 2:
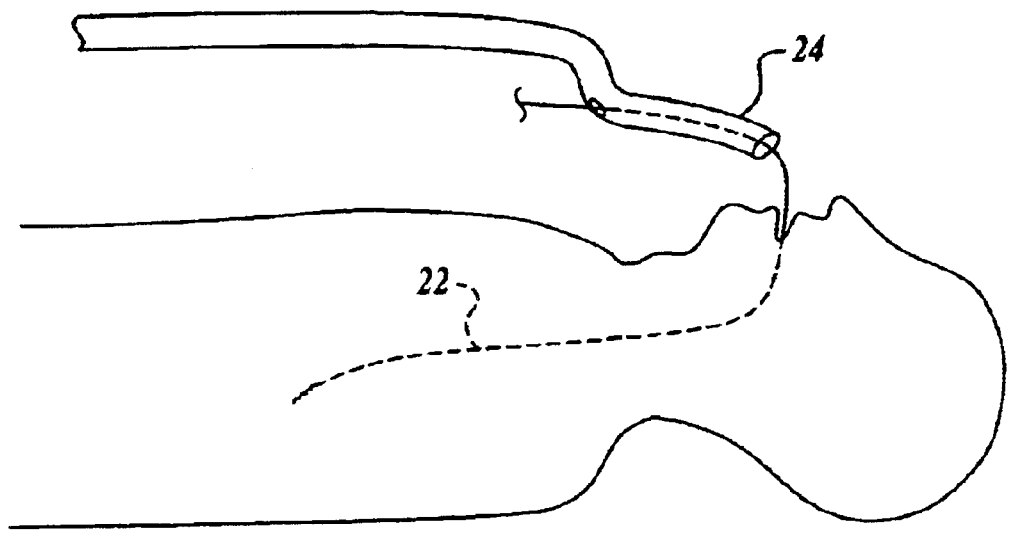
FIG. 2 illustrates a patient undergoing a catheter-based surgical procedure using a rapid exchange-type catheter.

FIGS. 1 and 2 illustrate a patient undergoing a minimally invasive surgical procedure that uses a guidewire. In FIG. 1, a guidewire 10 is positioned with its distal tip adjacent a tissue area to be treated within the patient's body. Typically, the guidewire 10 is routed through a lumen in an endoscope (not shown) such that the physician can see where the guidewire is to be placed. Once the guidewire is in the appropriate location, the physician removes the endoscope over the guidewire, thereby leaving the guidewire with its distal tip at the desired location. With the guidewire in the appropriate position, a catheter 20 can be routed over the guidewire in order to deliver a surgical device or treatment to the tissue in question. Such surgical devices can include balloons, stents, electro- or laser tissue cutting devices, aspirators or therapeutic delivery mechanisms, etc.

If the catheter 20 is a conventional type, it contains a lumen along it entire length through which the proximal end of the guidewire 10 is routed. In order to advance the catheter 20 into the patient, the guidewire 10 must have a length that is at least as long as the catheter 20 such that the physician can grasp the proximal end of the guidewire while advancing the catheter 20 into the patient. With this arrangement, it will be appreciated that the length of the guidewire that extends out of the patient may interfere with the physician's movements and make it more likely that the guidewire may be moved or dislodged and will have to be repositioned.

FIG. 2 shows a patient undergoing a minimally invasive surgical procedure using a "rapid exchange" type catheter that is fitted over a guidewire. In this embodiment, a guidewire 22 is positioned in the patient with its distal tip at a region of interest. Again, the guidewire is most often routed through a lumen in an endoscope to the desired position. The endoscope is then removed over the guidewire leaving the guidewire in place. A catheter 24 is then routed over the guidewire 22. A rapid exchange catheter has a guidewire lumen extends only along a portion of the length of the catheter. To route the catheter 24 over the catheter, the guidewire 22 is inserted through the shorter lumen and the proximal end of the guidewire 22 held securely in order to advance the catheter 24 into the patient. The advantage of the rapid exchange type catheter 24 is that the length of the guidewire 22 can be made significantly shorter than the type required for use with conventional catheters.

Figure 3:
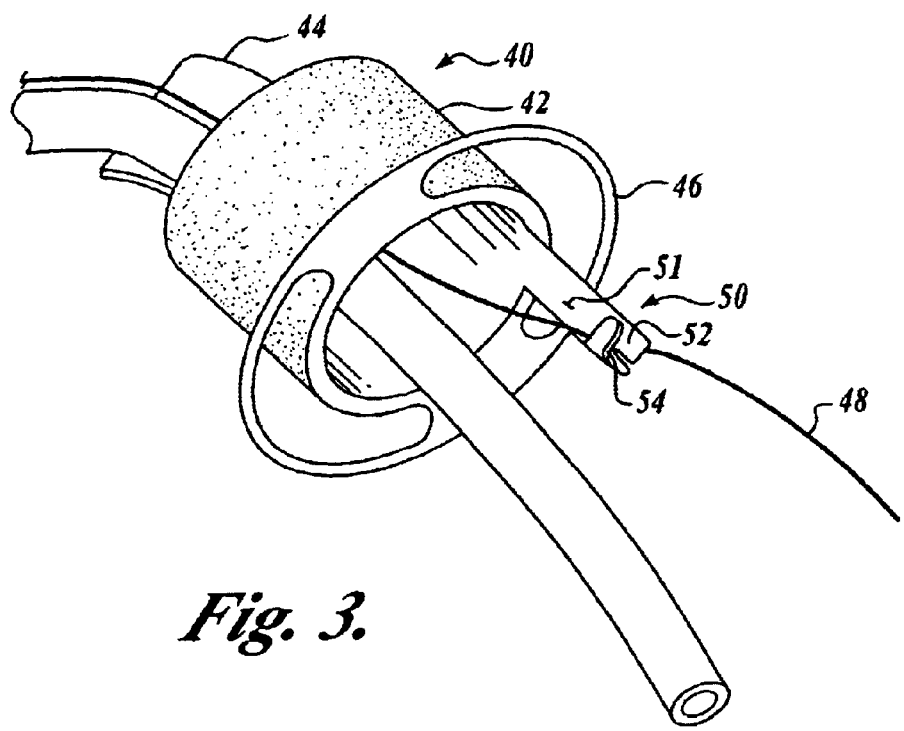
FIG. 3 illustrates a mouthguard having a locking device in accordance with one embodiment of the present invention.

Regardless of what type of catheter is used, it is important that the position of the guidewire remain substantially fixed as the physician is operating on the patient. FIG. 3 illustrates one embodiment of the present invention which is used to secure the position of a guidewire or other medical device that is inserted into the patient. A mouthguard 40 has a tube 42 that is positioned in the patient's mouth to provide access into the patient's alimentary or bronchial canals. The mouthguard may include a curved tongue 44 that extends distally from the tube 42 and operates to aid the passage of a catheter or endoscope into the patient's esophagus or trachea. In some embodiments, the outer surface of the tube 42 may be covered with a foam or other compressible material to protect the patient's teeth as surgical devices are inserted into the patient. Alternatively, the tube itself may be formed of a relatively soft material. A flange 46 is positioned at the proximal end of the tube 42 and has a diameter larger than the patient's mouth such that the mouthguard 40 cannot be accidentally swallowed by the patient.

To secure the position of a guidewire positioned in a patient, the mouthguard 40 includes a locking device 50 that is integrally formed with the mouthguard 40. The locking device 50 comprises a tab 51 that extends proximally from the opening of the tube 42. The tab 51 includes a slot 52 having a diameter that narrows to a width that is smaller than the diameter of the guidewire. The guidewire 48 can be secured in the slot 52 with a friction fit. Additionally, the locking device may include a tab 54 under which the guidewire can be passed in order to further secure the guidewire 48 to the locking device 50. The locking device 50 is not limited to securing guidewires but may contain other tabs or slots for securing the position of catheters or other medical devices placed into the patient's body. Other locking mechanisms may include clips, slots, hook and loop-type fasteners, or other mechanisms for securing the position of a medical device to the locking device.

Figure 4:
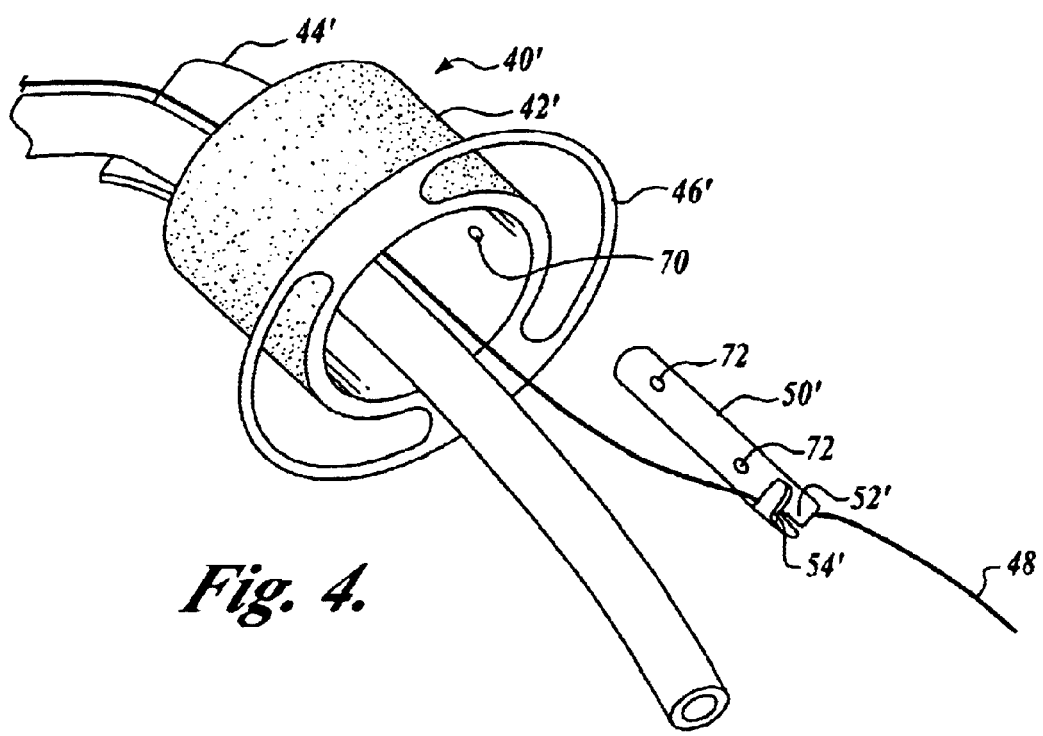
FIG. 4 illustrates a mouthguard having a locking device according to a second embodiment of the present invention.

FIG. 4 shows another embodiment of the mouthguard according to the present invention. A mouthguard 40' includes a tube 42' preferably covered with a compressible material such as foam. Extending from the distal end of the tube 42' is a curved tongue 44'. A flange 46' has a diameter that is larger than the patient's mouth and extends outwardly from the proximal end of the tube 42' such that the mouthguard 40' cannot be swallowed by a patient.

In this embodiment, the mouthguard includes a locking device 50' that is removably secured to the tube 42'. The locking device 50' has a slot 52' into which a guidewire 48 can be secured. In addition, the locking device may include a tab 54' under which the guidewire 48 may be passed in order to secure it to the locking device. The locking device 50' may include other mechanisms for securing the position of a number of medical devices passed through the mouthguard as indicated above. These other mechanisms may be in addition to or in lieu of the slot 52'.

In one embodiment of the invention, the locking device 50' is secured to the mouthguard using tabs 70 positioned on the tube 42' and corresponding holes or slots 72 positioned on the locking device 50' or vice versa. Alternatively, the locking device 50' could be secured to the mouthguard 40' using screws, interlocking channels, clips or other mechanisms for removably securing the two devices together.

While the preferred embodiment of the invention has been illustrated and described, it will be appreciated that various changes can be made therein without departing from the scope of the invention. The scope of the invention is therefore to be determined from the following claims and equivalents thereof.

The embodiments of the invention in which an exclusive property or privilege is claimed are defined as follows:

1. A mouthguard comprising:

a tube that is insertable into a patient's mouth and through which medical devices may be passed;

a flange extending outwardly from the tube to prevent the mouthguard from being swallowed; and an outwardly extending tab integrally formed with the mouthguard including means for securing the position of a medical guidewire passing through the tube.

2. The mouthguard of claim 1, wherein the means for securing a medical guidewire comprises a slot disposed within the tab therein into which the medical guidewire can be held with a friction fit.

3. The mouthguard of claim 1, wherein the means for securing a medical guidewire includes mechanisms for securing the position of two or more medical devices.

4. The mouthguard of claim 1, further comprising a compressible material surrounding the tube.

5. The mouthguard of claim 1, further comprising a tongue extending distally from the tube.

6. A mouthguard comprising:

a tube through which medical devices may be passed;

a flange extending outwardly from the tube to prevent the mouthguard from being swallowed;

an outwardly extending tab removably secured to the mouthguard including means for securing the position of a medical guidewire passing through the tube.

7. The mouthguard of claim 6, wherein the means for securing a medical guidewire comprises a slot into which the medical device can be held with a friction fit.

8. The mouthguard of claim 6, wherein the tab includes mechanisms for securing the position of two or more medical devices.

\* \* \* \* \*